(12) United States Patent
de Sousa Martins

(10) Patent No.: US 10,406,117 B2
(45) Date of Patent: Sep. 10, 2019

(54) WATER SOLUBLE LIPOPHILIC MATERIALS

(71) Applicant: Kemin Industries, Inc., Des Moines, IA (US)

(72) Inventor: Diogo de Sousa Martins, Sao Paulo (BR)

(73) Assignee: KEMIN INDUSTRIES, INC., Des Moines, IA (US)

(*) Notice: Subject to any disclaimer, the term of this patent is extended or adjusted under 35 U.S.C. 154(b) by 115 days.

(21) Appl. No.: 15/430,755

(22) Filed: Feb. 13, 2017

(65) Prior Publication Data
US 2017/0231913 A1 Aug. 17, 2017

Related U.S. Application Data

(60) Provisional application No. 62/295,258, filed on Feb. 15, 2016.

(51) Int. Cl.
A61K 9/127 (2006.01)
A61K 31/047 (2006.01)
A23L 3/00 (2006.01)
A23G 3/36 (2006.01)
A23G 3/40 (2006.01)
A23G 3/54 (2006.01)
(Continued)

(52) U.S. Cl.
CPC ............ A61K 31/047 (2013.01); A23G 3/36 (2013.01); A23G 3/40 (2013.01); A23G 3/54 (2013.01); A23G 4/06 (2013.01); A23L 2/52 (2013.01); A23L 3/00 (2013.01); A61K 9/127 (2013.01)

(58) Field of Classification Search
CPC ......... A61K 9/127; A61K 31/047; A23L 2/52; A23L 3/00; A23G 3/40; A23G 3/36; A23G 4/06; A23G 3/54
See application file for complete search history.

(56) References Cited

U.S. PATENT DOCUMENTS 5,569,464 A * 10/1996 Endo ................ A61K 9/127
424/450
7,446,101 B1 * 11/2008 Madhavi ............. A61K 9/19
514/58
8,591,942 B2 11/2013 Javeri et al.
(Continued)

FOREIGN PATENT DOCUMENTS

CN 102949343 A 3/2013
CN 103622912 A 3/2014
(Continued)

OTHER PUBLICATIONS

Junghans, A et al in Archives of Biochemistry and Biophysics, vol. 391, No. 2, pp. 160-164, 2001.*
(Continued)

Primary Examiner — Gollamudi S Kishore
(74) Attorney, Agent, or Firm — Nyemaster Goode P.C.

(57) ABSTRACT

The present invention is a water-soluble form of lipophilic molecules contained in liposomes. In one embodiment, the lipophilic molecule is crystalline lutein and the lutein-loaded liposomes are included in pharmaceutical products, medical devices, and dietary supplements industry, with potential for chewable tablets, fortification of beverages, effervescent tablets, uncoated tablets, nutritional bars, and functional foods in addition to cosmetic industry.

3 Claims, 2 Drawing Sheets

(51) Int. Cl.
A23G 4/06 (2006.01)
A23L 2/52 (2006.01)

(56) References Cited

U.S. PATENT DOCUMENTS

2004/0126886 A1\* 7/2004 Kan .................... A61K 9/1271
  435/458
2007/0269502 A1 11/2007 Pliura et al.
2015/0182460 A1\* 7/2015 Hong .................. A61K 9/0019
  424/450

FOREIGN PATENT DOCUMENTS

EP 2246327 A1 11/2010
WO 1990012565 A1 11/1990

OTHER PUBLICATIONS

International Searching Authority, "Search Report and Written Opinion," issued in connection with International Patent Application No. PCTUS17/17646, dated Jun. 2, 2017, 10 pages.

\* cited by examiner

WATER SOLUBLE LIPOPHILIC MATERIALS

RELATED APPLICATIONS

This application claims priority to U.S. Patent Application Ser. No. 62/295,258 filed Feb. 15, 2016, and incorporates the same herein in its entirety by this reference.

BACKGROUND OF THE INVENTION

The present invention relates generally to a method for producing a soluble form of lipophilic compounds such as carotenoids and, more specifically, to an emulsion containing high levels of liposome-encapsulated carotenoids, such as lutein and zeaxanthin, suitable for the use in pharmaceutical products, medical devices, and food industry.

Although no directives or guidelines exist regulating the indication of raw materials when developing a new pharmaceutical product, pharmaceutical grade substances should be used whenever possible.

Lutein is used in the pharmaceutical industry (in medical devices) and also as a coloring agent for a variety of foods and beverages (Scotter M J. 2011. Methods for the determination of European Union-permitted added natural colours in foods: a review. Food Additives and Contaminants. 28(5): 527-596). The natural form of lutein is in crystals. In consequence, it is insoluble in several dilution systems, which makes difficult its application in tableted products, medical devices and food related products. Soluble forms of crystalline lutein were developed, such as the so-called "Cold Water Soluble Lutein" (CWSLutein). However, this food-grade material presents some limitations, including formation of sediments that become visible after one or two days in solution. Sedimentation is probably due to other constituents of that raw material, which also include starch, glucose syrup and ascorbic acid. In addition, the presence of these substances hampers lutein release mainly due to the formation of a rigid polysaccharide-like structure (Amar I, Abraham A and Garti N. Solubilization Patterns of Lutein and Lutein Esters in Food Grade Nonionic Microemulsions. 2003. J. Agric. Food Chem. 51:4775-4781). Instability to light exposure is another problem of CWS-Lutein, as all products produced with this raw material need to be supplied in amber containers or kept in dark conditions. Therefore, the development of a pharmaceutical-grade, soluble, dispersible and stable carotenoid-containing raw material is an urgent need.

SUMMARY OF THE INVENTION

The present invention relates to a process for the manufacture of a form of lipophilic molecules, including lutein, which, among other characteristics, is easy to produce and has improved properties with regard to solubility including cold solvents (e.g. cold water). We performed studies by formulating phospholipids liposomes with lutein and a rigidity modifier to modify the absorption profile of the liposomes using only ingredients of pharmaceutical grade. Our work shows that (1) this new material has a good dispersibility in water without sedimentation after several months; (2) the presence of phospholipids, a rigidity modifier and a lipophilic environment facilitates the delivery of lutein into ocular/nasal/skin structures; (3) such formulations, containing phospholipids, a rigidity modifier and lutein, in case of oral use, allows a good dispersibility and much better absorption of lutein; (4) the presence of the rigidity modifier, such as glyceryl behenate having a melting point higher than 50° C., has the potential to modulate the rigidity of the final structure and therefore of the absorption profile. It is also important to consider that after sterilization the product appears clear and completely dispersed with non-evident sedimentation. Also, the new structure allows eliminating the food-grade excipients used in commercially available forms, contributing to a safer product.

This new form of lutein soluble in water is an important development for use in pharmaceutical products, medical devices, dietary supplements industry, with potential for chewable tablets, fortification of beverages, effervescent tablets, uncoated tablets, nutritional bars, and functional foods in addition to its cosmetic industry uses.

DESCRIPTION OF THE INVENTION

Figure 1:
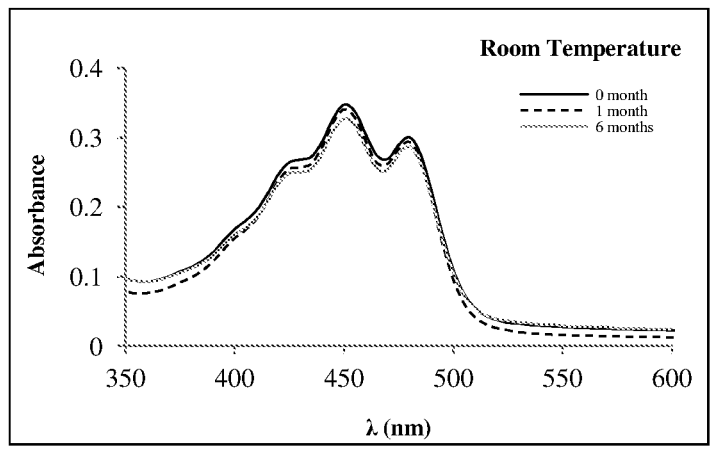
FIG. 1 is the WSLutein UV/Vis spectra in THF after 1 and 6 months at room temperature. The three characteristic peaks of lutein are visible.

The term "lipophilic molecule" as used herein refers to compounds which dissolve in lipids, fats, oils and non-polar solvents. The lipophilic molecule may be a pharmaceutically active agent, drug, imaging agent, therapeutic agent, diagnostic agent, compound, or composition. A non-limiting example of a lipophilic molecule is lutein. The lipophilic molecule may comprise between about 0.001% to 10% by weight of the liposome composition. Stated another way, the lipophilic molecule may comprise between about b.cde % to ab % by weight of the liposome composition, wherein a is either 0 or 1 and b, c, d and e are selected from 0, 1, 2, 3, 4, 5, 6, 7, 8 and 9 with the exceptions that all of b, c, d and e are 0 when a is 1 and not all of a, b, c, d and e are 0.

The term "liposomes" as used herein refers to single or multiple concentric lipid bilayers encapsulating an aqueous compartment. The liposome may include natural and/or synthetic lipids and surfactants. The liposomes trap the lipophilic molecule in the lipid membrane. The size of these nearly spherical lipid vesicles of the present invention can range between 50 and 450 nm. Stated another way, the size of the liposomes of the present invention range between about ab nm to about cde nm, wherein a is selected from 5, 6, 7, 8 and 9, b is selected from 0, 1, 2, 3, 4, 5, 6, 7, 8 and 9, c is selected from 0, 1, 2, 3 and 4, d is selected from 0, 1, 2, 3, 4 and 5 and e is selected from 0, 1, 2, 3, 4, 5, 6, 7, 8 and 9 except when c is 4 and d is 5 in which case it is 0. Of course not all of a, b, c, d and e can be 0.

The term "lipid film-forming liquid" as used herein refers to any lipid-containing liquids that form a film upon drying.

Non-limiting examples of lipid film-forming liquids include solubilized phospholipids, including lecithin and lysolecithin.

The term "solvent" as used herein refers to solvents in which the lipophilic molecule is soluble and which can be removed by evaporation. Non-limiting examples of solvents are chloroform, methanol and tetrahydrofuran.

The term "rigidity modifier" as used herein refers to a composition that modifies the rigidity and therefore the absorption profile of the liposomes of the present invention. Suitable rigidity modifiers include fats having medium to long chain fatty acid groups, such as lauric acid, myristic acid, palmitic acid, stearic acid, oleic acid, linoleic acid, ricinoleic acid, arachidic acid, behenic acid, tricosylic acid, lignoceric acid, pentacosylic acid, cerotic acid, heptacosylic acid, montanic acid, nonacosylic acid and melissic acid, with an elevated melting point. A non-limiting example of a rigidity modifier is glyceryl behenate.

EXAMPLE 1

Materials and Methods

Materials and reagents. Hydrogenated phosphatidylcholine was acquired from Lipoid GmbH, FloraGLO® lutein from Kemin Industries (Des Moines, Iowa) and glyceryl behenate from Gattefosse (Saint-Priest, France). CWS-Lutein was purchased from DSM (Heerlen, NL), trypan blue from Merck (Rahway, N.J.) and Brilliant blue from Sigma-Aldrich (St. Louis, Mo.). All organic solvents, chloroform, methanol and tetrahydrofuran (THF) were also purchased from Sigma-Aldrich while Quinine-HCl was from Acros Organics (Grand Island, N.Y.). All reagents needed for the cytotoxicity study were acquired from Lonza (Basel, CH): Dulbeco's modified Eagle's medium (DMEM), Nutrient Mixture F12 medium, Heat-inactivated fetal bovine serum (FBS), PBS $Ca^{2+}Mg^{2+}$ buffer, L-Glutamine, sodium pyruvate, HEPES, Penicillin and Streptomycin. Cell Proliferation Reagent WST-1 was purchased from Roche Applied Science (Penzberg, Del.).

WSLutein: Formulation development. For preparation of 4 liters of liposomes, hydrogenated phosphatidylcholine, FloraGLO® and glyceryl behenate (Table 1) were solubilized in 500 mL of chloroform and methanol (2:1 v/v) by heating at 30-35° C. to obtain a clear solution. To remove the solvents, the solution was dried under vacuum at 40° C.-50° C. by a Heidolph rotavapor, and a dry thin film was obtained after 1-2 hours. To assure the removal of all traces of solvent, the thin film was left under vacuum for at least 16 hours at room temperature, and gas chromatography was performed to confirm any residues were below 25 ppm. Finally, the film was hydrated by adding distilled water or phosphate buffer solution at 40-45° C. for at least 2-3 hours, under magnetic stirring, to obtain a cloudy dispersion. The cloudy dispersion was then homogenized by Ultraturrax homogenizer (Ika Works), at room temperature for 30 minutes and 2000-4000 rpm to obtain large vesicles, following micronization to a nano size range by extrusion using a large-scale microfluidizer at 50-60° C. and 1200 bar. This process was repeated at least 5 times. The phospholipids behenate beadlets were sterilized by steam sterilization at 121° C. for 15 minutes at 1 atm. Liposome size analysis was performed through dynamic light scattering (Nicomp 380 DLS) as described by Hupfeld et al (Hupfeld S, Holsaeter A M, Skar M, et al. Liposome size analysis by dynamic/static light scattering upon size exclusion-/field flow-fractionation. 2006. J Nanosci Nanotechnol., 6(9-10):3025-3031).

TABLE 1

Composition of WSLutein.

| Constituent | Content |
| --- | --- |
| Hydrogenated phosphatidylcholine | 2% |
| FloraGLO ® | 0.15% |
| Glyceryl behenate | 0.030% |

Dispersibility and sedimentation determination. These determinations were performed by visual evaluation throughout time.

UV/Vis spectra analysis. Lutein is insoluble in water, therefore THF was used to solubilize lutein and trace its UV/Vis spectra. Shortly, 1 mL of sample was transferred to a 10 mL volumetric flask and this was filled with distilled water. Then, 500 μL were transferred to a 25 mL volumetric flask and the pipette tip was washed with THF into the flask. The volume was brought to 25 mL with THF and the spectrum was traced from 300 to 750 nm in a UV/Vis spectrophotometer previously blanked with THF.

Cytotoxicity study. Cytotoxicity of WSLutein raw material was assessed by colorimetric analysis in Human Retinal Pigment Epithelial (ARPE-19) cells. Cells were cultured in a humidified atmosphere of 5% $CO_2$ and 95% air incubator at 37° C. and were grow in 1:1 mixture (vol:vol) of DMEM supplemented with 10% FBS, L-Glutamine (2 mM), sodium pyruvate (0.5 mM), HEPES (15 mM), penicillin (100 U/ml) and streptomycin (100 μg/ml). The cells were grown to an appropriate density and medium was replaced every 48-72 h.

Dye dilutions were chosen according to typical volumes of vitreoretinal surgery: 0.3 mL of dye are injected in the vitreous cavity (4 mL) and 8-10 mL/min of liquid flows during the procedure (BSS, ringer solutions, continuous perfusion, among others), reaching 600 mL per surgery (in a normal 60min surgery) and leading to dilutions of 1/15 (dye injection), 1/30 (t≈1 min), 1/60 (t≈1.5 min) and 1/20 (t≈3 min). A cataract surgery flow is estimated in 120 mL/min of liquid in the eye, resulting in much higher dilutions than those of vitreoretinal surgery.

WST-1 colorimetric assay was performed according to the manufacturer's recommendations to test in vitro cellular toxicity.

Briefly, APRE-19 cells were seeded at $10-12 \times 10^3$ cells/$cm^2$ in 96-well plates. After 18-22 h of growth, several dye dilutions (1/15, 1/30, 1/60 and 1/120) were applied to the cells for 30 or 120 minutes. After incubation, cells were washed three times with PBS $Ca^{2+}Mg^{2+}$ and then incubated overnight with fresh media +2% FBS. Cells were able to recover for 24, 48 or 72 h, fresh medium containing 10% WST-1 reagent was added and after 3 h of incubation, absorbance was measured at 450 nm using a TECAM 200 reader (TECAN Infinite M200 PRO), translating the level of metabolically active cells, which correlates with the number of viable cells. As a positive control, 0.02% sodium dodecyl sulfate (SDS) was used. Three independent experiments in triplicate, per concentration and time tested, were used. Data is reported as mean±standard deviation (SD), acquired using Excel—Microsoft Office.

Kemin Pharma dyes: Formulation development with WSLutein. WSLutein was used to formulate dyes with Brilliant blue (to simulate Retidyne™), with Trypan blue (to simulate Phacodyne™), and with both blue dyes (to simulate Doubledyne™), according to Table 2. The colors were blue, green and greenish blue, respectively.

TABLE 2

Composition of dyes with WSLutein or CWSLutein, in saline phosphate buffer.

| Dye | Constituent | Content |
|---|---|---|
| Retidyne ™ | CWSLutein | 2% (0.1% lutein) |
|  | Brilliant blue | 0.05% |
| Phacodyne ™ | CWSLutein | 1% (0.05% lutein) |
|  | Trypan blue | 0.04% |
| Doubledyne ™ | CWSLutein | 2% (0.1% lutein) |
|  | Brilliant blue | 0.05% |
|  | Trypan blue | 0.15% |
| WSRetidyne | WSLutein | 66% (0.1% lutein) |
|  | Brilliant blue | 0.05% |
| WSPhacodyne | WSLutein | 33% (0.05% lutein) |
|  | Trypan blue | 0.04% |
| WSDoubledyne | WSLutein | 66% (0.1% lutein) |
|  | Brilliant blue | 0.05% |
|  | Trypan blue | 0.15% |

Thermostability studies. WSLutein stability was tested for 1 and 6 months at room temperature and at 52° C. WSRetidyne, WSPhacodyne and WSDoubledyne formulations were tested for their stability at room temperature for 1 month. All vials containing the formulations were transparent but stored under no light exposure conditions and were performed in duplicate.

Photostability study. Photostability of WSLutein alone was studied. Furthermore, photostability of WSDoubledyne and Doubledyne™ (formulated with CWSLutein, as described in Table 2), were studied and compared, in amber and transparent glass vials. For these tests, a representative number of samples (3) were chosen to be exposed to light or to be exposed to non-light conditions, in the photostability chamber.

The photostability testing for a new drug substance or product is defined in the ICH Q1B Guideline. Shortly, the samples must be subjected to a light source for several hours in a validated photostability chamber. The photostability chamber used in this experiment is validated by *Autoridade Nacional do Medicamento e Produtos de Saúde I.P.* (*IN-FARMED*) for these types of studies. According to the ICH Q1B Guideline, samples have to be exposed side-by-side with a validated chemical actinometric system to ensure the minimum light exposure is attained, or for the appropriate duration of time when conditions have been monitored using calibrated radiometers/lux meters. Two 2% (w/v) solutions of Quinine-HCl were used as actinometric controls and were exposed to light or non-light conditions, with the latter being wrapped in aluminum foil. With this test, is possible to determine if the incidence time was enough to cause any possible degradation by measurement of $Abs_{400nm}$.

Dye samples and Quinine-HCl samples were inserted in the photostability chamber and subjected to the same conditions of UV and Visible light exposure for 48 hours. WSLutein or Doubledyne (CWS or WS) samples were then evaluated for possible product degradation according to defined parameters: appearance, color, pH and osmolality. For WSDoubledyne and Doubledyne™, also the UV-Vis spectra were analyzed on a spectrophotometer. pH and osmolality were assessed using a pH meter (Metrohm 713) and an Osmometer (Knauer, Berlin, DE). The decay in pH and osmolality in test and control samples was determined and results were expressed in percentage using Equation 1.

$$\% \text{ Decay} = 100 - (P_{sample} \times 100 / P_{Control})$$ Equation 1

Determination of the percentage of decay in a given parameter (P).

Results obtained through Equation 1 for pH and osmolality were compared between transparent (sample) and amber (control) vials (Tables 5 and 6). In addition, a comparison between light (sample) and no-light (control) exposure was performed for the same type of vials (Tables 5 and 6). To be compatible with ophthalmic application, pH must be within 6.0-7.4 (i.e. pH=6.7±0.7 or pH=6.7±10.45%) and osmolality must be within 250-380 mOsm/L (i.e. osmolality=315±65 mOsm/L or 315±20.63% mOsm/L). Therefore, and to establish a stringent criterion, results were validated when differences between conditions were less than 10%. Further details are provided in the Results section.

Cadaveric eyes study. A liposomic formulation very similar to WSLutein (1% phospholipids+0.05% FloraFLO) was tested in cadaveric eyes for its efficacy in dyeing intraocular membranes, which are the targets of Kemin Pharma products. Four cadaveric eyes were used as previously described[7] (according to the Research Guidelines of the ARVO and the tenets of the Declaration of Helsinki) and Retidyne and Phacodyne formulated with this liposomic solution instead of CWSLutein were tested. The staining intensity was determined using the grade scale from Table 3, by experienced surgeons in a blind experiment.

TABLE 3

Grade scale used for visual evaluation of dyeing efficacy in cadaveric eyes.

Staining grade

|  | Grade | | | | |
|---|---|---|---|---|---|
|  | 0 | 1 | 2 | 3 | 4 |
| Staining | No staining | Stained ¼ | Stained between ¼ and ½ | Stained between ½ and ¾ | Stained more than ¾ |

RESULTS

WSLutein formulation and analysis. A new form of soluble lutein is an important development for use in pharmaceutical products, medical devices, and other drug-like products. A new lutein raw material was formulated and produced containing phospholipids rigid beadlets (hydrogenated phosphatidylcholine), FloraGLO® lutein and glyceryl behenate, using only ingredients of high quality grade.

The quantity of lutein encapsulated in the phospholipids was chosen based on the actual Kemin Pharma products. Knowing that CWS lutein contains 5% of FloraGLO®, Kemin Pharma dyes contain between 0.05% and 0.1% of lutein. Therefore, the quantity of lutein chosen to be encapsulated was 0.15%, so formulations with the same lutein content would be prepared.

After solubilization of all components in organic solvents, these solvents were removed and a dry thin film was obtained. This film was then hydrated, micronized and sterilized.

After sterilization, the product appeared clear and completely dispersed with non-evident sedimentation. This raw material was then analyzed (Table 4) for its solubility and showed to have a good dispersibility in water without sedimentation after several days. Moreover, the sedimentation phenomenon observed after one week was less pronounced than the one seen in current CWSLutein. In summary, this new material showed to be more soluble, with less sedimentation propensity and to be more dispersible, when compared to CWSLutein. Additionally, particle size analysis after sterilization showed that lutein structure was maintained and the size was estimated between 200-800 nm. Osmolality and pH were also determined for this formulation and were in accordance to the Pharmacopoeial ocular physiological parameters (pH=7, osmolality=171-1711). The UV/Vis spectra was analyzed and showed the three peaks characteristic of Lutein (FIG. 1).

TABLE 4

Analysis of WSLutein raw material (0.15% FloraGLO ®) after production.

| Assay | Result |
|---|---|
| Appearance | Clear and no sedimentation |
| Color | Orange |
| Solubility in water | Good |
| Dispersibility in water | Good |
| Appearance after several days | Clear and no sedimentation |
| Dispersibility in water after several days | Good |
| Particle size | 200-800 nm |
| pH | 7.084 ± 0.01 |
| Osmolality | 250 ± 16.37 |
| UV/Vis spectra (max Abs) | Characteristic of lutein |

Figure 2:
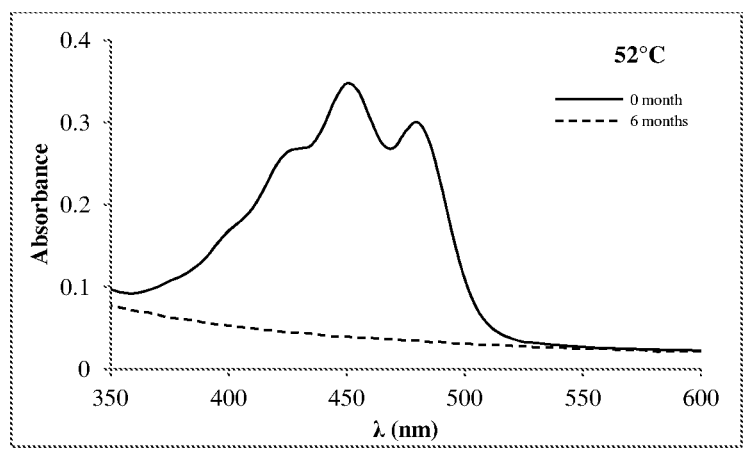
FIG. 2 shows the WSLutein UV/Vis spectra in THF after 6 months at 52° C. The three characteristic peaks of lutein are not visible after 6 months.

The stability of WSLutein was studied for 1 and 6 months at room temperature and results are shown in Table 5. FIG. 1 also shows the average UV/Vis spectra after 1 and 6 months. An accelerated study at 52° C. was also performed for 6 months (Table 6 and FIG. 2).

The new WSLutein raw material showed to be stable after 6 months storage at room temperature (FIG. 1 and Table 5). However, instability was observed at higher temperature (52° C.), since no lutein peaks were visible in the UV/Vis spectra (FIG. 2) and also a change in color was observed (Table 6).

TABLE 5

Stability study of WSLutein for 1 month at room temperature.

| Assay | 1 month | 6 months |
|---|---|---|
| Appearance | Clear and no sedimentation | Clear and no sedimentation |
| Color | Orange | Orange |
| pH | 7.104 ± 0.01 | 7.050 ± 0.041 |
| Osmolality | 270 ± 8.090 | 282 ± 3.333 |
| UV/Vis spectra (max Abs) | Characteristic of lutein | Characteristic of lutein |

TABLE 6

Stability study of WSLutein for 6 months at 52° C.

| Assay | 0 month | 6 months |
|---|---|---|
| Appearance | Clear and no sedimentation | Clear and no sedimentation |
| Color | Orange | Yellow |
| pH | 7.084 ± 0.01 | 6.72 ± 0.160 |
| Osmolality | 250 ± 16.37 | 278 ± 21.697 |
| UV/Vis spectra (max Abs) | Characteristic of lutein | No peaks between 350-600 nm |

The photostability of this formulation was also assessed in transparent and amber vials. The results are summarized in Tables 7 and 8 show no significant decay (<10%) in pH nor in osmolality between light-exposed and no-light exposed samples. Also, no differences were detected between transparent and amber vials. The results demonstrate that this new raw material is stable to light-exposure and may be stored in transparent vials.

TABLE 7

Photostability of WSLutein, comparing amber and transparent vials, subjected or not to light exposure.

| | Assay | Amber vials | | Transparent vials | |
|---|---|---|---|---|---|
| | | Light | No light | Light | No light |
| WSLutein | Appearance | Opaque | Opaque | Opaque | Opaque |
| | Color | Orange | Orange | Orange | Orange |
| | pH | 7.09 ± 0.012 | 7.12 ± 0.002 | 7.11 ± 0.004 | 7.13 ± 0.002 |
| | Osmolality | 266 ± 2.028 | 266 ± 5.508 | 268 ± 4.410 | 261 ± 19.743 |
| | UV/Vis spectra (max Abs) | Characteristic of lutein | Characteristic of lutein | Characteristic of lutein | Characteristic of lutein |

TABLE 8

% Decay of osmolality and pH for WSLutein: comparison between light and no-light conditions and amber and transparent vials.

| Parameter | Sample | Control | % Decay |
|---|---|---|---|
| pH | Amber vials light | Amber vials no-light | 0.33 |
| | Transparent vials light | Transparent vials no-light | 0.32 |
| | Transparent vials light | Amber vials light | −0.12 |
| | Transparent vials no-light | Amber vials no-light | −0.11 |
| Osmolality | Amber vials light | Amber vials no-light | −0.13 |
| | Transparent vials light | Transparent vials no-light | −2.55 |
| | Transparent vials light | Amber vials light | −0.50 |
| | Transparent vials no-light | Amber vials no-light | 1.88 |

Figure 3:
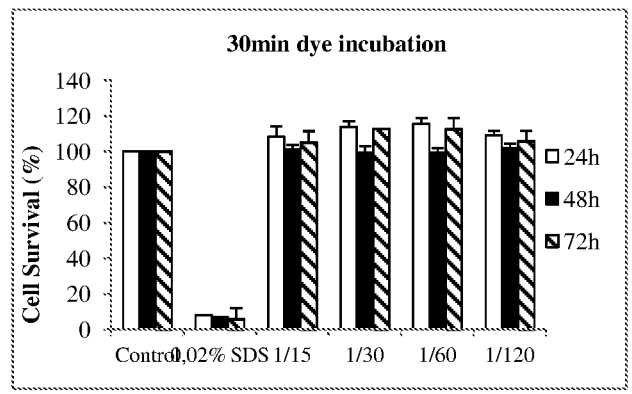
FIG. 3 is a chart of ARPE-19 cellular survival after 30min of WSLutein incubation and 24 h, 48 h and 72 h cell recovery. Cells without dye were used as control and 0.02% SDS was used as positive control. Standard errors from triplicate experiments are shown as error bars.
Figure 4:
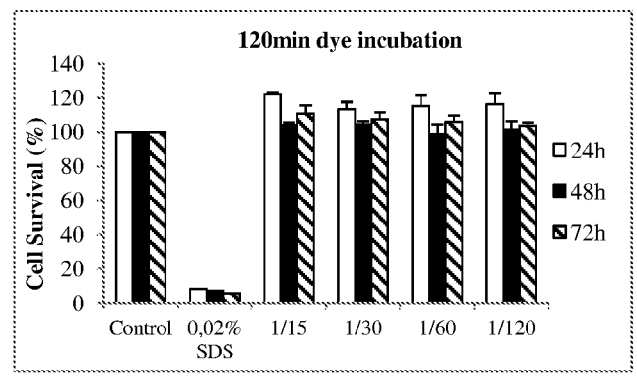
FIG. 4 is a chart of ARPE-19 cellular survival after 120min of WSLutein incubation and 24 h, 48 h and 72 h cell recovery. Cells without dye were used as control and 0.02% SDS was used as positive control. Standard errors from triplicate experiments are shown as error bars.

Cytotoxicity study. Cytotoxicity of WSLutein (dye dilutions 1/15, 1/30, 1/60 and 1/120) was assessed in vitro in ARPE-19 cells using WST-1 colorimetric assay by measuring absorbance at 450 nm. The results in FIGS. 3 and 4 show no cytotoxicity of this formulation for incubation of 30 min or 120 min with the dye dilutions and after 24, 48 or 72 h of cells recovery, since minimal difference in cell viability was observed between the control and dye-treated cells.

Figure 5:
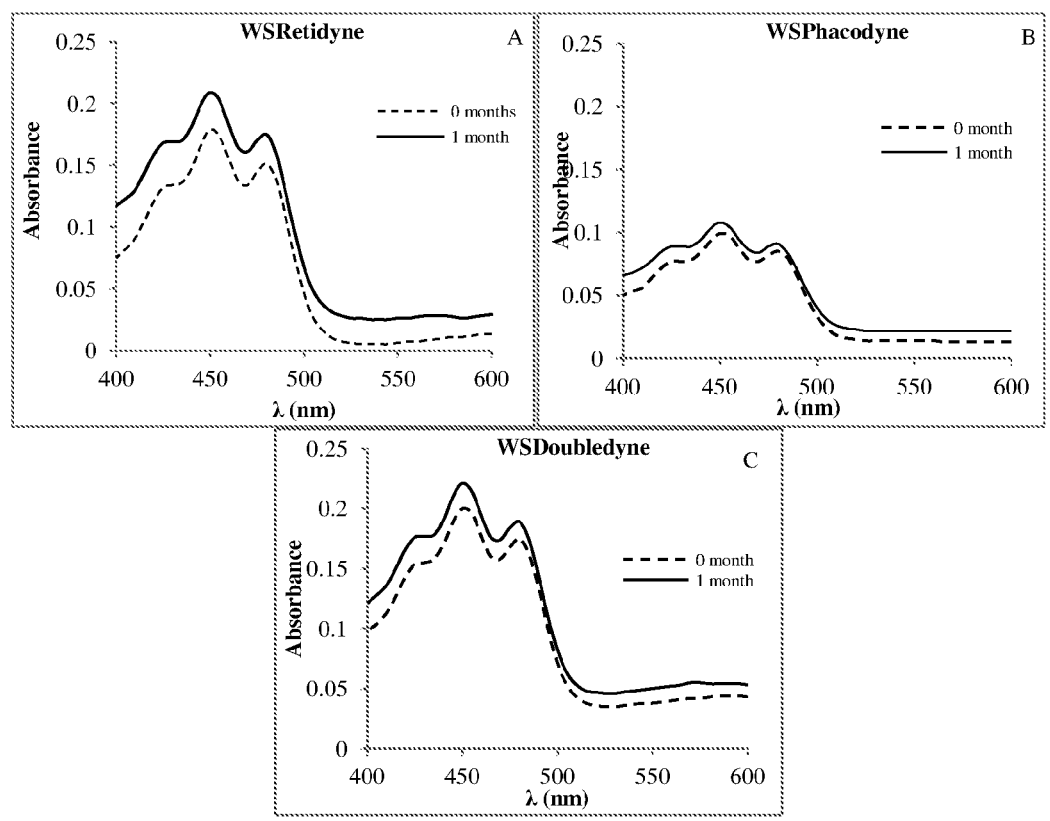
FIG. 5 shows the UV/Vis spectra of WSRetidyne (A), WSPhacodyne (B) and WSDoubledyne (C) at the beginning of the stability study and after 1 month at room temperature.

Analysis of dyes formulated with WSLutein. The new WSLutein raw material was used to formulate Doubledyne™, Retidyne™ and Phacodyne™ (see Table 2). These formulations were analyzed for their color, appearance, pH, osmolality and UV/Vis spectra (Table 9). Moreover, the stability of the formulations was studied for 1 month at room temperature and results show that they are stable for these conditions (Table 9 and FIG. 5).

TABLE 9

Analysis of Doubledyne, Retidyne and Phacodyne formulated with WSLutein.

| | Assay | 0 month | 1 month |
|---|---|---|---|
| WSDoubledyne | Appearance | No sediments | No sediments |
| | Color | Greenish blue | Greenish blue |
| | pH | 7,066 | 7,104 |
| | Osmolality | 277 | 281 |
| | UV/Vis spectra (max Abs) | Characteristic of lutein | Characteristic of lutein |
| WSRetidyne | Appearance | No sediments | No sediments |
| | Color | Green | Green |
| | pH | 7,054 | 7,075 |
| | Osmolality | 278 | 275 |
| | UV/Vis spectra (max Abs) | Characteristic of lutein | Characteristic of lutein |
| WSPhacodyne | Appearance | No sediments | No sediments |
| | Color | Blue | Blue |
| | pH | 7,023 | 7,058 |
| | Osmolality | 280 | 282 |
| | UV/Vis spectra (max Abs) | Characteristic of lutein | Characteristic of lutein |

The photostability of Doubledyne formulated with WSLutein was studied and compared to photostability of Doubledyne™ (with CWSLutein). Table 10 and 11 show the results of the comparative between transparent and amber vials.

TABLE 10

Photostability of Doubledyne formulated with WSLutein in comparison to the Doubledyne ™ (CWSLutein).

| | | Amber vials | | Transparent vials | |
|---|---|---|---|---|---|
| | Assay | Light | No light | Light | No light |
| WSDoubledyne | Appearance | No sediments | No sediments | No sediments | No sediments |
| | Color | Blue | Blue | Blue | Blue |
| | pH | 7.04 | 7.00 | 7.05 | 7.03 |
| | Osmolality | 259 | 266 | 264 | 271 |
| | UV/Vis spectra (Abs) | Characteristic of lutein | Characteristic of lutein | Characteristic of lutein | Characteristic of lutein |
| | $A_{452nm}$ | 0.155 | 0.173 | 0.165 | 0.165 |
| CWSDoubledyne | Appearance | No sediments | No sediments | No sediments | No sediments |
| | Color | Blue | Blue | Blue | Blue |
| | pH | 6.67 | 6.67 | 6.67 | 6.67 |
| | Osmolality | 376 | 379 | 389 | 387 |
| | UV/Vis spectra (max Abs) | Characteristic of lutein | Characteristic of lutein | Characteristic of lutein | Characteristic of lutein |
| | $A_{452nm}$ | 0.529 | 0.575 | 0.480 | 0.590 |

TABLE 11

Percentage of decay from CWSLutein product (CWSDoubledyne) to WSLutein product (WSDoubledyne) and from Light exposed to No light exposed vials.

| Parameter | Sample | Control | % Decay |
|---|---|---|---|
| pH | Amber vials light (WS) | Amber vials no-light (WS) | −0.52 |
| | Transparent vials light (WS) | Transparent vials no-light (WS) | −0.28 |
| | Amber vials light (CWS) | Amber vials no-light (CWS) | 0.09 |
| | Transparent vials light (CWS) | Transparent vials no-light (CWS) | 0 |
| Osmolality | Amber vials light (WS) | Amber vials no-light (WS) | 2.50 |
| | Transparent vials light (WS) | Transparent vials no-light (WS) | 2.46 |
| | Amber vials light (CWS) | Amber vials no-light (CWS) | 0.88 |
| | Transparent vials light (CWS) | Transparent vials no-light (CWS) | −0.69 |
| $A_{452nm}$ | Amber vials light (WS) | Amber vials no-light (WS) | 10.23 |
| | Transparent vials light (WS) | Transparent vials no-light (WS) | 0.10 |
| | Amber vials light (CWS) | Amber vials no-light (CWS) | 8.11 |
| | Transparent vials light (CWS) | Transparent vials no-light (CWS) | 18.75 |

The specifications used to verify quality of Kemin Pharma dyes formulated with CWSLutein must assure that pH and osmolality are fully compatible with the eye physiological parameters. Therefore, pH must be within 6.0-7.4 (i.e. pH=6.7±0.7 or pH=6.7±10.45%) and osmolality must be within 250-380 mOsm/L (i.e. osmolality=315±65 mOsm/L or 315±20.63% mOsm/L).

Although pH and osmolality are important characteristics of these formulations for ophthalmic application, absorbance at 452 nm is the most important parameter related to lutein stability, as it is completely dependent of lutein content. Specifications for commercial Doubledyne formulated with CWS predict that absorbance at 452 nm must be within 0.633-0.861 (i.e. 0.861±0.228 or 0.861±26.50%). To assess photostability, we considered a more stringent interval of 10% variation of absorbance between conditions to ensure we were accurately evaluating lutein stability.

The results summarized in Tables 10 and 11 show there are only significant decays (>10%) in absorbance at 452 nm for CWSDoubledyne when light-exposed transparent vials are compared to no-light exposed transparent vials. From Table 11, WSDoubledyne can be considered photostable as no significant decays were seen for any parameter.

Cadaveric eyes study. Retidyne and Phacodyne formulated with a very similar WSLutein liposomic solution, instead of CWSLutein, were evaluated in human cadaveric eyes in order to determine their efficacies in dying ocular membranes and structures. Results are listed in Table 12 and show a good staining capacity of Retidyne formulation to ILM, and of Phacodyne to the anterior capsule staining (the primary target structure).

TABLE 12

Cadaveric eyes study results for Retidyne and Phacodyne formulated with a liposomic solutions very similar to WSLutein.

| Solution | Grading | | | | | |
|---|---|---|---|---|---|---|
| Tissue | ILM* | | Vitreous | | AC* | |
| Eye tested | Eye 1 | Eye 2 | Eye 1 | Eye 2 | Eye 1 | Eye 2 |
| Phacodyne with liposomic lutein | 2 | 2 | 1 | 2 | 3 | 4 |
| Retidyne with liposomic lutein | 3 | 3 | 2 | 0 | 2 | 3 |

*AC—Anterior capsule, ILM—Internal limiting membrane

DISCUSSION

There is the need of developing a new water soluble lutein/zeaxanthin without the undesired behaviors of CWS-Lutein, commercialized by DSM Nutritional Products, Inc. Presently, several dyes are produced with this soluble CWS-Lutein. Unfortunately, this soluble form was shown to be unstable through time, as sediments were found after 1-2 days in solution, and also did not favor lutein dispersibility, mainly due to its very rigid polysaccharide-like material composition (Amar I, Abraham A and Garti N. Solubilization Patterns of Lutein and Lutein Esters in Food Grade Nonionic Microemulsions. 2003. J. Agric. Food Chem. 51:4775-4781). Additionally, manufacturers of vitamins/dietary supplements/medical devices products require materials that can withstand a wide range of tableting pressures and sterilization protocols, placing significant restrictions upon ingredients that can be used in the transformation of lutein. These same restrictions are believed to play a critical role in the bioavailability of lutein since the new method used must ensure the release of this molecule.

Therefore, a new raw material soluble in water, which does not sediment, enables lutein bioavailability and resists steam sterilization needed to be developed. This would not only be an advantage for proprietary dyes but also for all producers of tableted products, medical devices and food related products.

This paper describes the formulation and production processes that were developed to reach these goals and create WSLutein, a liposomic lutein (200 to 800 nm) that was shown to be stable and soluble in water. Moreover, the sedimentation phenomenon is less pronounced than the one seen in CWSLutein. The presence of phospholipids, glyceryl behenate and a lipophilic environment facilitates the delivery of lutein into ocular, nasal or skin structures and, in case of oral use, allows a good dispersibility and much better absorption of lutein. Furthermore, the presence of glyceryl behenate, having a melting point higher than 50° C., has the potential to modulate the rigidity of the final structure and therefore of the absorption profile.

In preliminary tests with dye formulations of WSLutein (combined with Trypan blue and/or Brilliant blue), these dyes showed to be stable through autoclaving and after 1 month at room temperature, as did WSLutein. Also, WSLutein raw material showed to be stable for 6 months at room temperature. Longer stability studies following ICH guidelines will be performed and will contribute to better understand the stability profile of this raw material. Sensibility to light exposure is another undesired characteristic of CWSLutein. In photostability studies, WSLutein (and dyes formulated with WSLutein) was shown to be photostable and this characteristic also supports the higher quality of this raw material. Another important issue in the pharmaceutical industry is the safety of the materials used and WSLutein showed no cytotoxicity in a retinal cell line, reinforcing the advantages of this new raw material.

WSLutein is therefore suggested for the use in pharmaceutical products, medical devices, and dietary supplements industry, with enormous potential for chewable tablets, fortification of beverages, effervescent tablets, uncoated tablets, nutritional bars, and functional foods in addition to its cosmetic industry uses.

More stability studies on this product are being performed as also, safety experiments with dyes formulated with WSLutein are being evaluated so registrations can be obtained (cytotoxicity, sensitization and irritation tests, as well as in vivo efficacy).

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

I claim:

1. A method of manufacturing liposomes, comprising the steps of dissolving lutein in an organic solvent to form a solution, wherein the lutein is present in concentrations in the range of 0.001%-10%, mixing the solution into a solution of phospholipid and glyceryl behenate in an organic solvent to form a mixture, drying the mixture to form a lipid film, hydrating the lipid film, homogenizing the hydrated lipid film to form liposomes, and sterilizing the obtained liposomes.

2. The method of claim 1, wherein the lutein comprises lutein crystals.

3. The liposomes of claim 1 comprising a pharmaceutically acceptable excipient.

* * * * *